United States Patent [19]
Lentz et al.

[11] Patent Number: 4,594,445
[45] Date of Patent: Jun. 10, 1986

[54] CARBONYLATION PROCESS FOR THE PRODUCTION OF AROMATIC ACIDS AND DERIVATIVES THEREOF

[75] Inventors: Carl M. Lentz, Mt. Carmel; James R. Overton; David D. Cornell, both of Kingsport, all of Tenn.

[73] Assignee: Eastman Kodak Company, Rochester, N.Y.

[21] Appl. No.: 689,419

[22] Filed: Jan. 7, 1985

[51] Int. Cl.$^4$ ............................................. C07C 69/76
[52] U.S. Cl. ................................... 560/103; 562/406; 564/132; 546/261; 548/531; 549/71; 560/100
[58] Field of Search ............... 560/103, 100; 562/406; 564/132; 546/261; 548/531; 549/71

[56] References Cited

U.S. PATENT DOCUMENTS 3,733,354  5/1973  Cassar et al. ........................ 560/103
3,952,028  4/1976  Jezic .................................... 560/103
3,988,358  10/1976  Heck .................................... 560/103
4,506,092  3/1985  Lentz et al. ......................... 560/103
4,507,493  3/1985  Lentz et al. ......................... 560/103

OTHER PUBLICATIONS

Beringer et al, *J.A.C.S.*, 81, 342 (1959).
Davidson et al, *J. Chem. Soc. (A)*, 1968, pp. 1616–1617.

*Primary Examiner*—Paul J. Killos
*Attorney, Agent, or Firm*—Clyde L. Tootle; J. Frederick Thomsen

[57] ABSTRACT

The present invention provides a process for the preparation of aryl carboxylic acids and derivatives thereof by the carbonylation of diaryliodonium salts. The diaryliodonium salts are reacted with carbon monoxide and water or an alcohol or amine in a base reaction medium having a p$K_b$ greater than about 8.

13 Claims, No Drawings

CARBONYLATION PROCESS FOR THE PRODUCTION OF AROMATIC ACIDS AND DERIVATIVES THEREOF

DESCRIPTION

This invention relates to a novel catalytic carbonylation process for the production of aromatic acids, esters, and/or amides. More particularly, this invention relates to a novel process for the carbonylation of a diaryliodonium salt in the presence of water, an alcohol, or an amine, in a base reaction medium having a $pK_b$ greater than about 8.

The preparation of carboxylic acid esters by carbonylation process is well known in the art. One such process is described in U.S. Pat. No. 3,988,358 whereby carboxylic acid esters or amides are obtained from aryl halides and substituted derivatives thereof by the reaction of the particular starting material with an alcohol or primary or secondary amine and carbon monoxide in the presence of a palladium catalyst.

Another carbonylation process discloses that diaryliodonium salts can be carbonylated to aromatic esters and amides by reacting the diaryliodonium salt with carbon monoxide and an alcohol in the presence of a palladium catalyst. See, for example, Nippon Kagaku Kaishi, 1982, No. 2, pp. 236–241.

Another carbonylation process is described in Davidson et al (J. Chem. Soc. (A), 1968, pp. 1616–17) discloses the reaction of diphenyliodonium bromide and carbon monoxide at 190 atmospheres in methanol at 100° C. in the absence of a catalyst. However, without a catalyst the process only provided methylbenzoate in yields of about 35 to 50%.

Therefore, it would be an advance in the state of the art to provide a process for carbonylation of diaryliodium salts to prepare organic aromatic acids, esters of amides in high yields without a noble metal catalyst.

In accordance with the present invention, it has now been found that the diaryliodonium salt can be carbonylated to the desired aromatic acid, ester and/or amide or derivative thereof by reaction with water, an aliphatic alcohol or a primary amine in a base reaction medium. Moreover, the carbonylation reaction specifically and selectively carbonylates only the diaryliodonium salt and does not carbonylate the aromatic iodide by-product present in the reaction medium. This aromatic iodide is a recyclable by-product which can be used for the regeneration of the diaryliodonium starting material to provide a more efficient and inexpensive process.

The diaryliodonium salt employed as a starting material in the process of the present invention has the following chemical formula:

wherein Ar and Ar' are carbocyclic or heterocyclic aromatic groups having from about 5 to about 20 carbon atoms and having one or more rings. Such groups can be, for example, toluene, benzene, naphthalene, pyridine, thiophene, pyrrole, and the like. Preferably, Ar and Ar' are the same group.

Moreover, the aryl groups of the diaryliodonium salt can be connected by means of a carbon or heteroatom bridge, as exemplified by the following formulas:

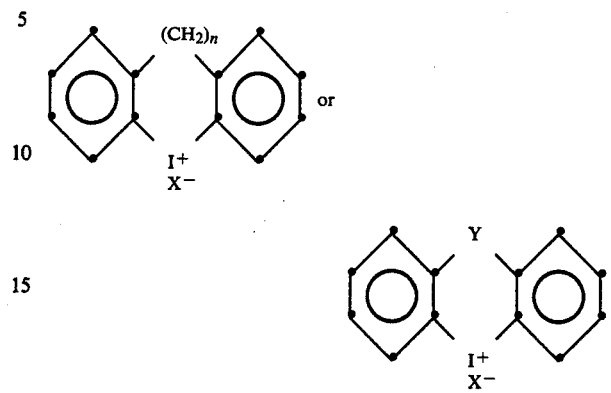

wherein n can be 1, 2 or 3, and Y can be O, S, or N and X represents a weak acid anion.

The aryl groups of the diaryliodonium salt can be substituted or unsubstituted. Such substituents include, for example, halides, alkyl groups having up to about 12 carbon atoms, vinyl groups, carboxylic acid groups, carboxylic ester groups, ether groups, nitrogen groups and the like.

Examples of weak acid anions can be, for example, acetate, trihaloacetate such as weak acid triiodoacetate, p-toluenesulfonate, benzenesulfonate, hydroxide, iodide, bromide, boron tetrafluoride, and the like.

Preferred examples of such diaryliodonium salt include, for example, diphenyliodonium bromide, ditolyliodonium acetate, ditolyliodonium iodide, diphenyliodonium iodide, diphenyliodonium acetate, and the like.

The diaryliodonium salts employed in the process of the present invention can be prepared by the methods described by Beringer et al in J.A.C.S., 81, 342 (1959), the disclosure of which is incorporated herein by reference in its entirety.

The diaryliodonium salt is reacted with water or an aliphatic alcohol having up to about 12 carbon atoms or primary amine having up to about 12 carbon atoms in the presence of carbon monoxide, and in a base reaction medium having a $pK_b$ greater than about 8, preferably about 8.0 to about 11.0, most preferably about 9.0 to about 10.0. Where water is employed as the reactant, an aromatic carboxylic acid is produced; when an alcohol is employed, the corresponding aromatic ester is produced; and when an amine is employed, the corresponding amide is produced.

More particularly, the aromatic esters are produced by the reaction of a diaryliodonium salt with an aliphatic alcohol. The aliphatic alcohol which is employed in the present process may be monofunctional or multifunctional. Therefore, glycols and other polyols are suitable, as are glycol esters, glycol ethers, and other such derivatives. Preferably, the alcohol comprises a lower alkanol such as an alkanol having up to about 12 carbon atoms, ethylene glycol, propylene glycol, neopentyl glycol, ethylene glycol monoacetate, mixtures thereof, and the like.

Suitable primary amines which may be employed in the preparation of amides by the process of the present invention include both aliphatic amines and aromatic amines. Suitable primary aliphatic amines include those having up to about 12 carbon atoms, such as monoethylamine, mono-n-butylamine, mono-2-ethylhexylamine, octylamine, dodecylamine, and the like. Suitable aromatic amines include aniline, substituted anilines, and the like. Multifunctional primary amines, such as the phenylenediamines, also may be used in the present process.

The catalytic carbonylation reaction of the present invention is conducted in the presence of carbon monoxide, which is employed in amounts such that the total reaction pressure is in the range of about 100 psig (about 700 kPa) to about 500 psig (about 3500 kPa). Superatmospheric pressure may be advantageous when a volatile reactant is employed or when an increase in the rate of reaction is desirable. Pressures from 100 pressure up to about 200 psig (about 1750 kPa) are most preferred.

The process of the present invention can be conducted at temperatures of about 50° C. to about 200° C. Preferably, the temperature of the reaction is in the range of about 75° C. to 100° C., most preferably 80° C.

The reaction is carried out in a reaction medium having a $pK_b$ greater than about 8.0, preferably about 8.0 to about 11.0. The base used can be an organic base or an inorganic base. The base is present in an amount of about 1 mole iodonium salt to 1 mole base to about 1 mole iodonium salt to 10 mole base which provides a reaction medium having a $pK_b$ of at least 8, preferably about 1 mole iodonium salt to 3 moles base. Bases which have been particularly useful are inorganic bases such as, for example, sodium hydroxide, potassium hydroxide, sodium carbonate, and the like. Organic bases which are particularly useful are, for example, trialkyl amines such as trimethylamine, triethylamine, tributylamine, triphenylamine, and the like.

Inert coordinating solvents may be employed, but are not necessary. Such solvents include, for example, tetrahydrofuran, acetonitrile, and the like. In preparing aromatic esters by the reaction of a diaryliodonium salt with carbon monoxide and an alcohol, the alcohol can be employed as solvent. Likewise, when preparing amides, the amine can be employed as solvent.

The aryl iodide by-product can be removed from the reaction system by distillation and then employed in the preparation of the diaryliodonium salt starting material. In contrast to prior art processes, the aryl iodide in the present process is not consumed by carbonylation to an aromatic acid or derivative thereof and is therefore available for use in the preparation of the diaryliodonium salt starting material. This improvement represents a more efficient and cost effective process in that the iodide-containing product is preserved and recycled. In this manner, the relatively expensive component of the reaction system need not be supplied to the reaction process in considerable quantities on a continuous basis, as was necessary with prior art processes, but can be prepared by using the aryl iodide process by-product.

The process of the present invention provides an efficient, novel and economical process for providing products which are useful as intermediates in the synthesis of polyesters, such as polyethylene terephthalate, and other useful polymeric materials.

The invention will be further illustrated by the following Examples although it will be understood that these Examples are included merely for purposes of illustration and are not intended to limit the scope of the invention.

EXAMPLES 1-10

The following Examples illustrate the carbonylation of a ditolyliodonium salt in the presence of an alcohol, a base and carbon monoxide to produce the corresponding p-methylbenzoate ester and iodotoluene. The particular anion, alcohol, base employed in each example are indicated below in Table I. The base was present in a concentration of 3.0 millimoles per millimole of iodonium salt.

In each Example, a 100 ml three-neck, round bottom flask was fitted with a reflux condenser, a thermometer, magnetic stirrer, and a gas dispersion tube. To the described apparatus were added 1.0 millimoles of the indicated diaryliodonium salt, 3.0 millimoles of the indicated base, and 50 ml of the indicated alcohol. While carbon monoxide was fed beneath the surface of the reaction mixture at the indicated total pressure, the reaction mixture was heated to the indicated temperature and was held at that temperature for the indicated period of time. The resulting mixture was cooled to 25° to 30° C. and was filtered through a Celite pad. Water (250 ml) was added to the filtrate, and the resulting mixture was extracted three times with 50 ml of diethyl ether. The ether extracts were combined and dried over magnesium sulfate. The solvent was removed *in vacuo* to yield a light yellow oil. GLPC analysis, employing authentic samples for comparisons, indicated the presence of p-methyltoluate (p-2-hydroxyethyltoluate in Example 5) and p-iodotoluene as the only products of reaction.

The results of these Examples are given in Table I.

TABLE I

| Ex. | X | Alcohol | Temperature (°C.) | Pressure (psig) | Base | Conversion (%) | Time (hrs) |
| --- | --- | --- | --- | --- | --- | --- | --- |
| 1 | OAc⁻ | Methanol | 80 | 100 | NaOH | 91 | 2 |
| 2 | OAc⁻ | Methanol | 80 | 100 | Na₂CO₃ | 91 | 6 |
| 3 | OAc⁻ | Methanol | 60 | 200 | Et₃N | 48 | 1 |
| 4 | OAc⁻ | Methanol | 60 | 200 | Na₂CO₃ | 47 | 1 |
| 5 | I⁻ | Ethylene Glycol | 80 | 100 | NaOH | 48 | 2 |
| 6 | I⁻ | Methanol | 80 | 100 | Na₂CO₃ | 85 | 1 |
| 7 | I⁻ | Methanol | 80 | 100 | Et₃N | 78 | 1 |
| 8 | BF₄⁻ | Methanol | 50 | 100 | KOH | 97 | 3 |
| 9 | I⁻ | Methanol | 50 | 100 | Na₂CO₃ | 22 | 2 |
| 10 | I⁻ | Methanol | 50 | 100 | Et₃N | 9 | 2 |

Repeating these examples using water in place of the alcohol provided the p-methylbenzoic acid in place of the p-methylbenzoate esters. Likewise, repeating these examples using monomethyl amine provided the p-methylbenzoamide in place of the p-methylbenzoate esters.

COMPARATIVE EXAMPLES 11-13

These Comparative Examples demonstrate the advantages of the present invention. In particular, these Compartive Examples demonstrate that the iodotoluene by-product of the above Examples is carbonylated in the presence of a base, but is not carbonylated in the absence of a base or in the presence of an acid.

In Example 11 about 1.0 millimole of p-iodotoluene and 40 ml of the indicated alcohol and no base were provided to the above-described reaction apparatus. In Example 12 about 10 millimole hydrochloric acid was added to the reaction to provide an acid reaction medium. In Example 13 about 3.0 millimole sodium hydroxide was added to the reaction mixture to provide a base reaction medium having a pK$_b$ greater than 8. In Example 14 about 10 millimole of a weak base pyridine was added to the reaction mixture to provide a base reaction medium having a pK$_b$ of less than 8. While carbon monoxide was fed beneath the surface of the reaction mixture so that the indicated total pressure was obtained, the reaction mixture was heated to the indicated temperature and was held at that temperature for the indicated period of time. Upon completion of reaction, the reaction mixture was worked up as described above. The results are given below in Table II.

TABLE II

| Comp. Ex. | Alcohol | Added | Temperature (°C.) | Pressure (psig) | Conversion (%) | Time (hrs) |
|---|---|---|---|---|---|---|
| 11 | Methanol | Nothing | 80 | 100 | 0 | 2 |
| 12 | Ethylene Glycol | 20% HCl | 80 | 100 | 0 | 1.5 |
| 13 | Methanol | 20% NaOH | 80 | 100 | 91 | 2 |
| 14 | Methanol | 20% pyridine | 80 | 100 | 0 | 2 |

These results clearly demonstrate that conversion of the diaryliodonium salt to the corresponding ester occurred in the presence of the base while no reaction occurred in the presence of an acid, a weak base, or without the base.

The invention has been described in detail with particular reference to preferred embodiments thereof, but it will be understood that variations and modification can be effected within the spirit and scope of the invention.

We claim:

1. A process for the preparation of compounds of the formula

ArCOR or ArCNHR', wherein R represents H or an aliphatic moiety having up to about 12 carbon atoms and R' represents an aliphatic moiety having up to about 12 carbon atoms, said process comprising reacting a diaryliodonium salt of the formula

wherein Ar and Ar' each independently represents a carbocyclic or heterocyclic aromatic moiety having about 5 to about 20 atoms in the ring or rings thereof and X represents a weak acid anion, with (i) carbon monoxide and (ii) a member selected from the group consisting of water, an aliphatic alcohol having up to 12 carbon atoms or a primary amine having up to about 12 carbon atoms in a base reaction medium having a pK$_b$ greater than about 8.0.

2. The process of claim 1 wherein Ar and Ar' are the same aromatic moiety.

3. The process of claim 2 wherein Ar and Ar' represent moieties derived from toluene, benzene, naphthalene, pyridine, thiophene, or pyrrole.

4. The process of claim 3 wherein X$^-$ represents acetate, trihaloacetate, p-toluenesulfonate, benzenesulfonate, hydroxide, iodide, bromide, or boron tetrafluoride.

5. The process of claim 4 wherein said alcohol comprises a lower alkanol, ethylene glycol, propylene glycol, neopentyl glycol, ethylene glycol monoacetate, or a mixture thereof.

6. The process of claim 5 wherein the reaction temperature is about 100° C. to about 700° C.

7. The process of claim 6 wherein the reaction system further comprises a base having a pK$_b$ of about 8.0 to about 11.0.

8. The process of claim 7 wherein said base comprises triethylamine or sodium carbonate.

9. A process for the preparation of aromatic esters which comprises reacting at a temperature of about 100° to about 200° C. a diaryliodonium salt of the formula

wherein Ar represents a moiety derived from toluene, benzene, naphthalene, pyridine, thiophene, or pyrrole and X represents a weak acid anion comprising acetate, trihaloacetate, p-toluenesulfonate, benzenesulfonate, hydroxide, iodide, bromide, or boron tetrafluoride, with carbon monoxide and an alcohol comprising an alkanol containing up to 12 carbon atoms, ethylene glycol, propylene glycol, neopentyl glycol, ethylene glycol monoacetate, or a mixture thereof in a base reaction medium having a pK$_b$ of about 9.0 to about 10.0.

10. The process of claim 9 wherein Ar represents a moiety derived from toluene or benzene.

11. The process of claim 10 wherein said alcohol comprises methanol, ethylene glycol, ethylene glycol monoacetate, or a mixture thereof.

12. The process of claim 11 wherein the reaction temperature is about 100° to about 150° C.

13. The process of claim 12 wherein said base comprises triethylamine or sodium carbonate.

* * * * *